United States Patent [19]

Tani et al.

[11] Patent Number: 5,237,074
[45] Date of Patent: Aug. 17, 1993

[54] PROCESS FOR PRODUCTION OF METHYLTETRAHYDROPHTHALIC ANHYDRIDE

[75] Inventors: Shoji Tani, Nishinomiya; Kenji Nishio, Otsu; Kiyoshi Iwahashi, Yamatokoriyama; Shigeki Hashimoto, Kyoto, all of Japan

[73] Assignee: New Japan Chemical Co., Ltd., Kyoto, Japan

[21] Appl. No.: 780,567

[22] Filed: Oct. 21, 1991

Related U.S. Application Data

[63] Continuation of Ser. No. 353,624, Mar. 8, 1989, abandoned.

[30] Foreign Application Priority Data

Jul. 10, 1987 [JP] Japan .................................. 62-173492
Jun. 17, 1988 [JP] Japan .................................. 63-150631

[51] Int. Cl.$^5$ .......................................... C07D 307/77
[52] U.S. Cl. ....................................... 549/240; 549/248
[58] Field of Search .......................... 549/248; 548/240

[56] References Cited

U.S. PATENT DOCUMENTS

| | | | |
|---|---|---|---|
| 3,927,038 | 12/1975 | Liakumovich et al. | 260/346.3 |
| 4,332,733 | 6/1982 | Samejima et al. | 549/240 |
| 4,560,773 | 12/1985 | Telschow | 549/240 |
| 4,564,687 | 1/1986 | Telschow | 549/240 |

FOREIGN PATENT DOCUMENTS 56-039082 4/1981 Japan .
62-294675 12/1987 Japan .

OTHER PUBLICATIONS

Parham et al. in "J.A.C.S." 75, pp. 2065–2069 (1953).
Concise and Chemical dictionary by Bennett (3rd edition), p. 390 (1974).

*Primary Examiner*—Thurman K. Page
*Assistant Examiner*—Jyothsna Venkat
*Attorney, Agent, or Firm*—Armstrong, Westerman, Hattori, McLeland & Naughton

[57] ABSTRACT

This invention provides a process for producing methyltetrahydrophthalic anhydride characterized in that maleic anhydride and a C$_5$ fraction are subjected to Diels-Alder reaction in the presence of a radical polymerization inhibitor and oxygen. According to the process of this invention, formation of gels as byproduct is substantially completely inhibited.

10 Claims, No Drawings

PROCESS FOR PRODUCTION OF METHYLTETRAHYDROPHTHALIC ANHYDRIDE

This application is a continuation of application Ser. No. 353,624, filed Mar. 8, 1989, now abandoned.

TECHNICAL FIELD

This invention relates to a process for producing methyltetrahydrophthalic anhydride without formation of a gel-like polymer and with high efficiency.

BACKGROUND TECHNOLOGY

It is well known that methyltetrahydrophthalic anhydride can be produced by Diels-Alder reaction between maleic anhydride and a $C_5$ fraction.

For example, 3-methyltetrahydrophthalic anhydride (hereinafter referred to briefly as 3Me—THPA) is obtained when trans-1,3-pentadiene is used as the $C_5$ fraction and 4-methyltetrahydrophthalic anhydride (hereinafter referred to briefly as 4Me—THPA) is obtained when isoprene is used as said $C_5$ fraction.

The $C_5$ fraction to be used for the production of such methyltetrahydrophthalic anhydride need not be in a purified form and is commonly used in the form of a crude fraction as the diene component. This is due to the fact that, while the trans-1,3-pentadiene, for example, separated from the $C_5$ fraction produced by naphtha cracking and the like usually contains olefins, diolefins and paraffins such as cis-1,3-pentadiene, pentanes and pentenes as impurities, trans-1,3-pentadiene substantially selectively participates in the Diels-Alder reaction.

While the use of such a crude fraction is thus economically advantageous, it entails the disadvantage that mainly cis-1,3-pentadiene and other olefins (and also a portion of trans-1,3-pentadiene or isoprene) tend to copolymerize with maleic anhydride to form a gel-like byproduct.

The hitherto-proposed methods for overcoming such a problem include the addition of a radical polymerization inhibitor such as hydroquinone (Japanese Examined Patent Publication No. 5537/1970), the use of benzene, toluene, xylene or the like as a diluent (Japanese Unexamined Patent Publication No. 92932/1979) and the concomitant use of a different kind of cyclic acid anhydride (Japanese Unexamined Patent Publication No. 39082/1981).

However, even the use of a radical polymerization inhibitor does not necessarily result in a complete prevention of the formation of a gel-like byproduct and, moreover, discolors the product. The use of a diluent which is poor in reactivity necessitates a step for removing and recovering the diluent after completion of the reaction, and entails an economic disadvantage. When a different cyclic acid anhydride is used in combination, the unit production is decreased and, therefore, the method is not advantageous economically.

DISCLOSURE OF THE INVENTION

It is an object of this invention to provide a novel and commercially useful process for producing methyltetrahydrophthalic anhydride which does not entails formation of a gel-like polymer.

The diligent research undertaken by the inventors of this invention for overcoming the above-mentioned disadvantages of the prior art led to the finding that the presence of a radical polymerization inhibitor and oxygen in the reaction system results in an effective inhibition or suppression of gel-like polymer formation. This invention has been made based on the above finding.

Thus, this invention provides a process for producing methyltetrahydrophthalic anhydride characterized by subjecting maleic anhydride and a $C_5$ fraction to Diels-Alder reaction in the presence of a radical polymerization inhibitor and oxygen.

In accordance with this invention, the formation of a gel-like polymer can be inhibited or suppressed and a methyltetrahydrophthalic anhydride of high purity can be produced in nearly quantitative yield by conducting the Diels-Alder reaction in the presence of a radical polymerization inhibitor and oxygen.

Furthermore, the methyltetrahydrophthalic anhydride produced by the process of this invention is generally only faintly colored or colorless.

The process for producing methyltetrahydrophthalic anhydride according to this invention is characterized in that maleic anhydride and a $C_5$ fraction are subjected to Diels-Alder reaction wherein a radical polymerization inhibitor and oxygen are present in the reaction system.

The $C_5$ fraction to be used in this invention may for example be crude trans-1,3-pentadiene or isoprene, or a mixture thereof.

The crude trans-1,3-pentadiene commercially available contains trans-1,3-pentadiene, typically in a proportion of about 10 to 80 percent by weight, and additionally contains cis-1,3-pentadiene, pentanes, pentenes and so on. In the process of this invention, the composition of such a crude fraction is not particularly critical if the desired product can be obtained. Thus, even if the trans-1,3-pentadiene content of the $C_5$ fraction is as low as about 10 to 25 percent by weight and, for this reason, if the proportion of cis-1,3-pentadiene and the like which are likely to form a gel-like product is relatively large, the process of this invention characteristically provides the desired methyltetrahydrophthalic anhydride in high yield while suppressing the formation of the gels. In this invention, such a crude $C_5$ fraction is reacted with maleic anhydride in the per se conventional manner, but it is important that both a radical polymerization inhibitor and oxygen are present in the reaction system.

Thus, the radical polymerization inhibitor and oxygen synergistically contribute remarkably to the suppression of the formation of a gel-like polymer byproduct in the course of reaction.

Incidentally, in the heretofore known processes for preparing methyltetrahydrophthalic anhydride of this type, since the inflammable $C_5$ fraction is used, it is common practice to conduct replacement of air with an inert gas such as nitrogen gas not only during transportation of the starting materials but also within the reaction system. Thus, it has been considered that the presence of oxygen should be excluded.

As procedures for allowing oxygen to be present in the reaction system, the following methods (1) and (2) may be exemplified.

(1) The method wherein the reaction system atmosphere is replaced with an oxygen-containing gas (hereinafter referred to as the replacement method)

(2) The method wherein the gas phase and/or liquid phase within the reaction system is aerated with an oxygen-containing gas (hereinafter referred to as the aeration method). This method can be classified, according to the phase which is aerated, into the gas phase aeration method and the liquid phase aeration method.

The term 'oxygen-containing gas' mentioned in regard to (1) and (2) above means a gaseous mixture of oxygen with an inert gas, such as nitrogen gas, helium gas, argon gas, etc., which is prepared for enhanced operation safety. The oxygen concentration of such a gaseous mixture is not so critical but for avoiding the risk of combustion and explosion and for suppressing the formation of gels and discoloration of the product, it is appropriately about 50 ppm to 8% (by volume), preferably about 1000 ppm to 4% (by volume) and, more preferably about 3000 ppm to 2% (by volume).

The proper rate of passing such an oxygen-containing gas in the aeration method is suitably determined in correlation with other reaction conditions.

Generally, when such a gas is to be passed through the gas phase of the reaction system, its flow rate may be about 0.04 to 0.8 ml/min., preferably about 0.05 to 0.6 ml/min., and more preferably about 0.06 to 0.5 ml/min., all calculated as oxygen in the oxygen-containing gas, per mole of the starting material maleic anhydride. On the other hand, when the liquid phase is to be aerated, the flow rate of gas may be about 0.0005 to 0.10 ml/min., preferably about 0.001 to 0.09 ml/min., and more preferably about 0.003 to 0.08 ml/min., all calculated as oxygen in said oxygen-containing gas, per mole of maleic anhydride. By way of illustration, when a nitrogen gas containing 4% by volume of oxygen is used in the gas phase aeration method, a rate of about 1 to 20 ml/min. per mole of the starting material maleic anhydride is suitable. When a nitrogen gas containing 1% by volume of oxygen is used in the liquid phase aeration method, a rate of about 0.05 to 10 ml/min. per mole of maleic anhydride is suitable. Generally, the lower the reaction temperature, the smaller the amount of oxygen required tends to be.

These methods for introducing oxygen into the reaction system may be employed singly or in combination, and the specific procedures are not limited to those described above so far as the object of this invention is achieved.

As examples of the radical polymerization inhibitor which can be used in this invention, there may be mentioned phenolic radical polymerization inhibitors such as 2,6-di-tert-butyl- 4-methylphenol, 2,6-dicyclopentyl-4-methylphenol, 2,2'-methylenebis(4-ethyl-6-tert-butylphenol), 4,4'-methylenebis(2,6-ditert-butylphenol), 4,4'-thiobis(3-methyl-6-tert-butylphenol), hydroquinone, p-tert-butylcatechol, p-benzoquinone, butylhydroxytoluene, etc. and these inhibitors can be used singly or in combination.

The amount of such radical polymerization inhibitor is not particularly critical if the effect thereof can be produced, but it is generally in the range of about 10 to 2000 ppm (on a weight basis; the same applies hereinafter) and preferably about 50 to 1500 ppm, based on the theoretical yield of methyltetrahydrophthalic anhydride. If the amount of said inhibitor is less than the above range, its inhibitory effect on polymer formation will not be sufficient. The use of said inhibitor in excess of the range will not result in any further enhancement of the effect and hence is economically disadvantageous.

In the process of this invention, the concomitant use of any of the organosulfur compound's mentioned under (a) through (e) below and alkyl phosphites as an auxiliary polymerization inhibitor results in a further enhanced inhibitory effect on polymer formation and a marked inhibition of coloration of the resulting methyltetrahydrophthalic anhydride. (a) Compounds of the general formula $$R^1-S_x-R^2$$

wherein $R^1$ and $R^2$ are the same or different and each represent an alkyl group of 1 to 20 carbon atoms, a hydroxycarbonylalkyl group of 2 to 20, preferably 2 to 6, carbon atoms and the corresponding $C_1-C_{20}$ alkyl ester group, i.e. ($C_1-C_{20}$ alkoxy)carbonyl-$C_1-C_{19}$ alkyl, preferably ($C_1-C_{20}$ alkoxy)carbonyl-$C_1-C_5$ alkyl, and the corresponding di($C_1-C_{20}$ alkyl)amido group, i.e. di($C_1-C_{20}$ alkyl)aminocarbonyl-$C_1-C_{19}$ alkyl, preferably di($C_1-C_{20}$ alkyl)aminocarbonyl-$C_1-C_5$ alkyl, an aryl group which may optionally be substituted, particularly a phenyl group which may optionally be amino- or halogen-substituted, an aralkyl group, particularly benzyl, or benzoyl; x represents an integer of 1 to 3.

(b) Compounds of the general formula

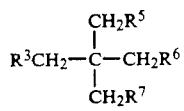

wherein $R^3$ represents $-OCO(CH_2)_nSR^4$; $R^5$, $R^6$ and $R^7$ each represent a hydrogen atom, an alkyl group of 1 to 2 carbon atoms or $-OCO(CH_2)_nSR^4$; $R^4$ represents a hydrogen atom or an alkyl group of 1 to 20 carbon atoms; and n represents an integer of 1 to 5.

(c) Cyclic thioethers (d) Trialkyl ($C_1-C_{20}$) trithiophosphites (e) Tetraalkyl($C_1-C_4$) thiuram mono- or polysulfides.

As specific examples of said compounds under (a), there may be mentioned dimethyl dithiodipropionate, dithiodipropionic acid, alkylthioacetic acid and alkylthiopropionic acids and alkyl esters thereof (i.e., general formula: $R-S(CH_2)_m-COOR'$ wherein R is a $C_1-C_{20}$ alkyl group; $R'$ is a hydrogen atom or a $C_1-C_{12}$ alkyl group; and m is 1 or 2), p-aminophenylmercaptoacetic acid, benzylthioacetic acid, butyl thiobenzoate ($C_6H_5CO-S-C_4H_9$), dibenzyl sulfide, dicetyl thiodipropionate, N,N'-dilaurylthiodipropionic acid amide, dilauryl thiodipropionate, dimethyl thiodipropionate, diphenyl sulfide, dibutyl sulfide, distearyl thiodipropionate, thioanisole, thiodipropionic acid, thiodiacetic acid, dithiodiacetic acid and so on. As the compounds under (b), there may be mentioned pentaerythritol tetra(3-mercaptopropionate), pentaerythritol tetrathioglycolate, trimethylolethane tri(3-mercaptopropionate), trimethylolpropane tri(3-mercaptopropionate) and so on. Among the above-mentioned cyclic, thioethers under (c) are thiophene, 1,4-dithiadiene and so on. As said trialkyl trithiophosphites under (d) above, there may be mentioned trilauryl trithiophosphite and so on. Among said tetralkylthiuram mono- or polysulfides under (e) above are tetramethylthiuram disulfide, tetramethylthiuram monosulfide, tetraethylthiuram disulfide, tetraethylthiuram monosulfide, tetrabutylthiuram disulfide, tetrabutylthiuram monosulfide and so on. In addition to the above-mentioned compounds under (a) through (e), other compounds such as stannic acid thioesters, e.g. dioctyltin bisisooctylmercaptoacetate etc., 2-mercaptobenzothiazole, dibenzothiazyl disulfide, 1,3-diphenylthiourea, methylenebisthioacetic acid, methylenebisthiopropionic acid, thiodipropionate polyesters (general formula:

St—(TD—G)$_p$—TD—St, wherein St is a C$_{18}$H$_{37}$ group;

G is —OCH$_2$CH$_2$O—, —O—C(CH$_3$)$_2$—O— or

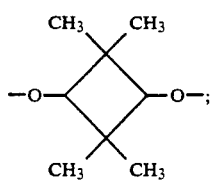

TD is —OOC(CH$_2$)$_2$—S—(CH$_2$—COO—; p is 1 or 2), etc. can also be employed. Of these organosulfur compounds, diesters of thiodipropionic acid, particularly the diesters thereof with C$_4$-C$_{18}$ higher aliphatic alcohols, are the most desirable.

As said alkyl phosphites, there may be mentioned trimethyl phosphite, triethyl phosphite, tributyl phosphite, trinonyl phosphite, tridecyl phosphite, dimethylphenyl phosphite, octyl diphenyl phosphite, dihexyl phenyl phosphite, nonyl diphenyl phosphite, triphenyl phosphite, trinonylphenyl phosphite and so on.

These alkyl phosphites are effective for preventing the formation of byproduct polymer and for preventing coloration of the product. However, when the product methyltetrahydrophthalic anhydride is to be subjected to isomerization reaction for use as a curing agent for epoxy resin, the alkyl phosphites tend to inhibit this isomerization reaction. Therefore, organosulfur compounds are more preferably used in the invention.

Though the amounts of such organosulfur compound and/or alkyl phosphites is not particularly critical, the total amount should be generally about 10 to 2000 ppm (on a weight basis; the same applies hereinafter) and preferably in the range of 50 to 1500 ppm based on the theoretical yield of methyltetrahydrophthalic anhydride. If the amount is less than the above range, the effect of addition of such organosulfur compound or alkyl phosphites will be insufficient, while the amount beyond the range would not lead to any marked improvement in the effect.

The process for producing methyltetrahydrophthalic anhydride according to this invention is usually carried out as follows.

Thus, a mixture of maleic anhydride with a radical polymerization inhibitor (and if necessary an auxiliary polymerization inhibitor) is first made into a molten state. Then, using an inert gas (for example, nitrogen gas) containing oxygen, a predetermined amount of oxygen is introduced into the reaction system according to said replacement method and/or aeration method, and a C$_5$ fraction is added for reaction in an amount corresponding to at least one mole, preferably 1.0 to 1.5 moles, of trans-1,3-pentadiene or isoprene per mole of maleic anhydride. The reaction pressure may range from atmospheric pressure to about 10 kg/cm$^2$. Generally, the range of atmospheric pressure to about 1.5 kg/cm$^2$ is preferable in the case of the aeration method. The reaction temperature is generally not more than 65° C., preferably about 40° to 60° C. The reaction is conducted for about 10 minutes to about 10 hours. The reaction is continued until the conversion based on maleic anhydride substantially reaches 100%.

The cis-1,3-pentadiene and other olefins contained in crude trans-1,3-pentadiene may be distilled off from the reaction system in the course of reaction, or may be separated as a volatile fraction together with unreacted trans-1,3-pentadiene from the reaction mixture by atmospheric distillation, flash distillation or the like after completion of the reaction. Thus, the product methyltetrahydrophthalic anhydride is given as a residue obtained by distillation of volatile fraction.

The methyltetrahydrophthalic anhydride thus obtained does not include said gel-like polymer, and can be isomerized to a product which is liquid at room temperature for use as a curing agent for epoxy resin. This product is also of great use as the acid component of unsaturated polyester resins.

EXAMPLES

The following examples are intended to illustrate this invention in further detail.

In the respective examples, the amounts of radical poymerization inhibitors and auxiliary polymerization inhibitors are invariably the amounts (expressed in ppm, by weight) based on the theoretical yield of methyltetrahydrophthalic anhydride. The C$_5$ fraction used in the respective examples was substantially free of dissolved oxygen by nitrogen gas treatment.

EXAMPLE 1

3Me—THPA was produced by the replacement method. Thus, a 1000 ml pressure-resistant autoclave previously filled with nitrogen gas (oxygen concentration 5 ppm, by volume; the same applies hereinafter) was charged with 98 g of maleic anhydride, 500 ppm of p-tert-butylcatechol by way of radical polymerization inhibitor, and 500 ppm of diphenyl sulfide by way of auxiliary polymerization inhibitor and the charge was melted by heating at 50° to 55° C. Then, the gas phase (about 930 ml) of the reaction system was replaced with nitrogen gas containing 0.6 volume % of oxygen under stirring. Thereafter, 374 g of crude trans-1,3-pentadiene having the following composition was continuously added at 50 to 55° C. over a period of 4 hours and, then, the reaction was carried out at 70° C. for 30 minutes. At this time, the internal pressure of the reaction system was 4 kg/cm$^2$.

| | | |
|---|---|---|
| Trans-1,3-pentadiene | 20.0% | by weight |
| Cis-1,3-pentadiene | 15.0 | " |
| Isoprene | 0.5 | " |
| Cyclopentadiene | 1.2 | " |
| Dicyclopentadiene | 0.4 | " |
| Cyclopentene | 12.1 | " |
| 2-Methylbutene-2 | 6.2 | " |
| Trans-pentene-2 | 3.0 | " |
| Cis-pentene-2 | 2.2 | " |
| n-Pentane | 18.6 | " |
| Cyclopentane | 16.5 | " |
| Other unidentified components | 4.3 | " |

After completion of the reaction, the volatile fraction was distilled off at 85° C. under atmospheric pressure and, then, under reduced pressure to give 165 g of 3Me—THPA. Thereafter, this product was dissolved in ether and the degree of contamination with insoluble matter was investigated. As a result, no gel formation was found.

EXAMPLE 2

The production of 3Me-THPA by the replacement method was carried out in the same manner as in Example 1 except that 1000 ppm of dibutyl sulfide was used as the auxiliary polymerization inhibitor and the internal atmosphere of the reaction system was replaced with nitrogen gas containing 0.1 volume % of oxygen, whereby 165 g of 3Me-THPA was obtained. The investigation revealed no gels in this product.

EXAMPLE 3

The production of 3Me—THPA by the replacement method was carried out in the same manner as in Example 1 except that 800 ppm of dilauryl thiodipropionate was used as the auxiliary polymerization inhibitor and the internal atmosphere of the reaction system was replaced with nitrogen gas containing 0.8 volume % of oxygen, whereby 165 g of 3Me—THPA was obtained. The investigation revealed no gels in the product.

EXAMPLE 4

4Me—THPA was produced by the replacement method. Thus, a 1000 ml pressure-resistant autoclave previously filled with nitrogen gas was charged with 98 g of maleic anhydride, 200 ppm of p-tert-butylcatechol by way of radical polymerization inhibitor and 500 ppm of dibutyl sulfide by way of auxiliary polymerization inhibitor and the charge was melted at 50° to 55° C. After the internal atmosphere of the reaction system was replaced with nitrogen gas containing 0.4 volume % of oxygen, 75 g of isoprene was continuously fed over a period of 4 hours and the reaction was carried out to completion at 50° to 55° C. After completion of the reaction, the volatile matter was distilled off under reduced pressure at 80° C. to give 164 g of 4Me-THPA. The investigation revealed no gels in this product.

EXAMPLE 5

3Me—THPA was produced by the gas phase aeration method. Thus, the air in a 300-ml four-necked flask equipped with a stirrer, thermometer, condenser, a dropping funnel for feeding crude trans-1,3-pentadiene, and an unreactive fraction recovery vessel was replaced with nitrogen and, then, the flask was charged with 98 g of maleic anhydride, 500 ppm of p-tert-butylcatechol by way of radical polymerization inhibitor and 1000 ppm of dilauryl thiodipropionate as auxiliary polymerization inhibitor. The charge was melted at 50° to 55° C. and after the internal atmosphere was replaced with nitrogen gas, nitrogen gas containing 4% of oxygen was passed through the gas phase at a rate of 10 ml/min throughout the reaction period. Under this atmosphere, 374 g of crude trans-1,3-pentadiene of the same composition as that used in Example 1 was continuously added at 50° to 55° C. over a period of 4 hours. During the reaction, major portion of unreactive fractions was distilled off from the reaction system. After completion of addition, the reaction was conducted at 70° C. for 30 minutes. After completion of the reaction, the reaction mixture was distilled at 85° C. under atmospheric pressure and, then, under reduced pressure to remove the volatile fraction. In this manner, 164 g of 3Me—THPA was obtained. The investigation revealed no gels in the product.

EXAMPLE 6

The production of 3Me—THPA by the gas phase aeration method was carried out in the same manner as in Example 5 except that 300 ppm of p-tert-butylcatechol was used as the radical polymerization inhibitor and 300 ppm of dilauryl thiodipropionate as the auxiliary polymerization inhibitor, whereby 165 g of 3Me—THPA was obtained. The investigation revealed no gels in the product.

EXAMPLE 7

The production of 3Me—THPA by the gas phase aeration method was carried out in the same manner as in Example 5 except that 500 ppm of trilauryl phosphite was used as the auxiliary polymerization inhibitor to give 165 g of 3Me—THPA. The investigation revealed no gels in the product.

EXAMPLE 8

3Me—THPA was produced by the liquid phase aeration method. Thus, the air in a 300 ml four-necked flask similar to the one used in Example 5 was replaced with nitrogen and, then, the flask was charged with 98 g of maleic anhydride, 300 ppm of p-tert-butylcatechol by way of auxiliary polymerization inhibitor and 800 ppm of dilauryl thiodipropionate by way of auxiliary polymerization inhibitor and the charge was melted at 60° C. Then, the internal atmosphere of the reaction system was replaced with nitrogen gas, and thereafter nitrogen gas containing 1 volume % of oxygen was passed into the reaction mixture at a rate of 5 ml/min throughout the reaction. Under this atmosphere, 374 g of crude trans-1,3-pentadiene of the same composition as that used in Example 1 was continuously added at 60° C. for 4 hours. Major portion of unreactive fractions was distilled off from the reaction mixture in the course of reaction. Thereafter, the reaction mixture was treated in the same manner as in Example 5 to give 164 g of 3Me—THPA. The investigation revealed no gels in the product.

EXAMPLE 9

3Me—THPA was produced by a combination of replacement and gas phase aeration methods. Thus, the air in a 300 ml four-necked flask similar to the one used in Example 5 was replaced with nitrogen gas and, then, the flask was charged with 98 g of maleic anhydride, 200 ppm of p-tert-butylcatechol by way of radical polymerization inhibitor and 800 ppm of dilauryl thiodipropionate by way of auxiliary polymerization inhibitor and the charge was melted by heating at 50° to 55° C. After the internal atmosphere of the reaction system was replaced with nitrogen gas containing 0.5 volume % of oxygen under stirring, the reaction was conducted while the gas phase was aerated under the same conditions as in Example 5, whereby 164 g of 3Me—THPA was obtained. The investigation revealed no gels in the product.

EXAMPLE 10

3Me—THPA was produced by a combination of replacement and gas phase aeration methods. Thus, the procedure of Example 9 was repeated except that no auxiliary polymerization inhibitor was used and the gas phase was aerated with nitrogen gas containing 4% of oxygen, whereby 164 g of 3Me—THPA was obtained. The evaluation revealed no gels in the product.

EXAMPLE 11

3Me—THPA was produced by a combination of replacement and liquid phase aeration method. Thus, the reaction procedure of Example 8 was repeated except that the respective amounts of maleic anhydride, radical polymerization inhibitor p-tert-butylcatechol and auxiliary polymerization inhibitor dilauryl thiodipropionate were melted at 60° C. and the internal atmosphere was replaced with nitrogen gas containing 1 volume % of oxygen. Then, the same oxygen-containing nitrogen gas was introduced into the liquid phase at a rate of 5 ml/min. The procedure gave 164 g of 3Me—THPA. The investigation revealed no gels in the product.

EXAMPLE 12

3Me—THPA was produced by a combination of replacement and liquid phase aeration methods. Thus, the reaction procedure of Example 11 was repeated except that 800 ppm of 2,6-di-tert-butyl-4-methylphenol was used as the radical polymerization inhibitor to give 164 g of 3Me—THPA. The investigation revealed no gels in the product.

EXAMPLE 13

3Me—THPA was produced by a combination of replacement and liquid phase aeration methods. Thus, the reaction procedure of Example 11 was repeated except that 800 ppm of 4,4'-methylenebis(2,6-di-tert-butylphenol) was used as the radical polymerization inhibitor to give 164 g of 3Me—THPA. The investigation revealed no gels in the product.

COMPARATIVE EXAMPLE 1

3Me—THPA was produced in the absence of oxygen. Thus, the reaction procedure of Example 1 was repeated except that the gas phase was replaced with nitrogen gas (oxygen concentration 5 ppm, by volume) in lieu of nitrogen gas containing 0.6 volume % of oxygen to give 165 g of 3Me—THPA. The investigation of solubility of this product in ether revealed the presence of gels in a proportion of 4%.

COMPARATIVE EXAMPLE 2

3Me—THPA was produced by the replacement method in the absence of a radical polymerization inhibitor. Thus, the reaction procedure of Example 1 was repeated except that the internal atmosphere of the reaction system was replaced with nitrogen gas containing 0.05 volume % of oxygen and neither a radical polymerization inhibitor nor an auxiliary polymerization inhibitor was added. The procedure gave 165 g of 3Me—THPA. The investigation of solubility of this product in ether revealed the presence of gels in a proportion of 8%.

COMPARATIVE EXAMPLE 3

The reaction procedure of Example 1 was repeated except that neither a radical polymerization inhibitor nor an auxiliary polymerization inhibitor was used and the reaction was conducted in the absence of oxygen (replacement with nitrogen containing 5 ppm of oxygen as in Comparative Example 1). The procedure gave 164 g of 3Me—THPA. The investigation of solubility of this product in ether revealed the presence of gels in a proportion of 12%.

We claim:

1. A process for producing methyltetrahydrophthalic anhydride from maleic anhydride and a $C_5$ fraction, comprising the step of subjecting said maleic anhydride and said $C_5$ fraction to a Diels-Alder reaction in an oxygen-containing gas mixture comprising oxygen and an inert gas wherein the oxygen concentration is about 50 ppm to about 8% on a volume basis, at a temperature of at most 65° C., a pressure ranging from atmospheric pressure to about 10 kg/cm$^2$m, and in the presence of:
   (i) about 10 ppm to about 2000 ppm by weight based on the theoretical yield of methyltetrahydrophthalic anhydride of a phenolic radical polymerization inhibitor; and
   (ii) about 10 ppm to about 2000 ppm by weight based on the theoretical yield of methyltetrahydrophthalic anhydride of at least one auxiliary polymerization inhibitor selected from the group consisting of an organosulfur compound and an organophosphorus acid ester,
   wherein said organosulfur compound is selected from the group consisting of:
   (a) compounds of the formula $$R^1-S_x-R^2$$

wherein each of $R^1$ and $R^2$ is independently selected from the group consisting of: a $C_1$-$C_{20}$ alkyl, a $C_2$-$C_{20}$ hydroxycarbonylalkyl, a ($C_1$-$C_{20}$ alkoxy)carbonyl-$C_1$-$C_{19}$ alkyl, a di($C_1$-$C_{20}$ alkyl)aminocarbonyl-$C_1$-$C_{19}$ alkyl, an unsubstituted aryl, an amino- or halogen-substituted aryl, an aralkyl, and benzoyl; and x is an integer of 1 to 3;
   (b) compounds of the formula $$R^3CH_2-\underset{\underset{CH_2R^7}{|}}{\overset{\overset{CH_2R^5}{|}}{C}}-CH_2R^6$$

wherein $R^3$ represents $-OCO(CH_2)_nSR^4$; each of $R^5$, $R^6$ and $R^7$ is independently selected from the group consisting of a hydrogen atom, a $C_1$-$C_2$ alkyl, and $-OCO(CH_2)_nSR^4$; $R^4$ is selected from the group consisting of a hydrogen atom and a $C_1$-$C_{20}$ alkyl; and n is an integer of 1 to 5;
   (c) thiophene or 1,4-dithiadiene;
   (d) tri($C_1$-$C_{20}$ alkyl) trithiophosphites; and
   (e) tetra($C_1$-$C_4$ alkyl) thiuram mono- or polysulfides,
   and wherein said alkyl phosphites is represented by the formula $$\begin{array}{c}R^aO\\R^bO-P\\R^cO\end{array}$$

wherein each of $R^a$, $R^b$ and $R^c$ is independently selected from the group consisting of a $C_1$-$C_{12}$ alkyl, phenyl, and phenyl substituted with a $C_1$-$C_9$ alkyl.

2. A process according to claim 1, wherein said $C_5$ fraction is crude trans-1,3-pentadiene or isoprene or a mixture thereof.

3. A process according to claim 1, wherein said Diels-Alder reaction is conducted after replacement of the internal atmosphere of the reaction system with said oxygen-containing gas mixture.

4. A process according to claim 1, wherein said Diels-Alder reaction is conducted while said oxygen-containing gas mixture is passed through the gas phase or liquid phase of the reaction system.

5. A process according to claim 4, wherein said oxygen-containing gas mixture is passed through the gas phase of the reaction system at a flow rate of 0.04 to 0.8 ml/minute, calculated as oxygen in said oxygen-containing gas mixture, per mole of maleic anhydride.

6. A process according to claim 4, wherein said oxygen-containing gas mixture is passed through the liquid phase of the reaction system at a flow rate of 0.0005 to 0.1 ml/minute, calculated as oxygen in said oxygen-containing gas mixture, per mole of maleic anhydride.

7. A process according to claim 1, wherein said phenolic radical polymerization inhibitor is at least one member selected from the group consisting of 2,6-di-tert-butyl-4-methylphenol, 2,6-dicyclopentyl-4-methylphenol, 2,2'-methylenebis (4-alkyl-6-tert-butylphenol), 4,4'-methylenebis-(2,6-di-tertbutylphenol), 4,4'-thiobis(3-methyl-6-tert-butylphenol), hydroquinone, p-tert-butylcatechol, p-benzoquinone and butylhydroxytoluene.

8. A process according to claim 1, wherein said $C_5$ fraction is used in an amount of 1.0 to 1.5 moles per mole of maleic anhydride, calculated as trans-1,3-pentadiene or isoprene.

9. A process according to claim 1, wherein said Diels-Alder reaction is carried out at a temperature of 40° to 60° C. and a pressure ranging from atmospheric pressure to about 10 kg/cm$^2$ until the conversion of maleic anhydride reaches substantially 100%.

10. A process according to claim 1, wherein said auxiliary polymerization inhibitor in said organosulfur compound.

* * * * *